US00PP29597P3

(12) United States Plant Patent
O'Connell

(10) Patent No.: US PP29,597 P3
(45) Date of Patent: Aug. 14, 2018

(54) ***ECHINOPSIS* PLANT NAMED 'MARDI GRAS'**

(50) Latin Name: *Echinopsis hybrida*
Varietal Denomination: Mardi Gras

(71) Applicant: Renee O'Connell, Escondido, CA (US)

(72) Inventor: Renee O'Connell, Escondido, CA (US)

(73) Assignee: Altman Specialty Plants, Inc., Vista, CA (US)

( * ) Notice: Subject to any disclaimer, the term of this patent is extended or adjusted under 35 U.S.C. 154(b) by 0 days.

(21) Appl. No.: 15/330,622

(22) Filed: Oct. 18, 2016

(65) Prior Publication Data

US 2018/0110167 P1 Apr. 19, 2018

(51) Int. Cl.
*A01H 5/02* (2018.01)
*A01H 5/04* (2018.01)

(52) U.S. Cl.
USPC ..... Plt./372
CPC ..... *A01H 5/02* (2013.01); *A01H 5/04* (2013.01)

(58) Field of Classification Search
USPC ..... Plt./372
See application file for complete search history.

*Primary Examiner* — Susan McCormick Ewoldt
(74) *Attorney, Agent, or Firm* — Cassandra Bright

(57) ABSTRACT

A new and distinct *Echinopsis* cultivar named 'Mardi Gras' is disclosed, characterized by distinctive large flowers of golden yellow with a vermillion mid-stripe. Flowering occurs more than once between Spring and Fall, continuing as late as August or September. Plants have a distinctive upright morphology. *Echinopsis* is an ornamental cactus, useful as an indoor ornamental plant and outdoors in warm climates.

3 Drawing Sheets

Latin name of the genus and species: *Echinopsis hybrida*.
Variety denomination: 'MARDI GRAS'.

BACKGROUND OF THE INVENTION

The new cultivar, *Echinopsis* 'Mardi Gras', was developed by the inventor, Renee O'Connell, as the result of a crossing made March 2012 as part of a planned breeding program. The seed parent variety is the unpatented proprietary variety referred to as *Echinopsis hybrida* 'Yel 08', a member of the Chamaelobivia group of *Echinopsis*. The pollen parent is the unpatented proprietary variety *Echinopsis hybrida* 'Wint 17', a member of the Lobivia group. *Echinopsis* 'Mardi Gras' was selected by the inventor, Renee O Connell, in April of 2013 from a group of seedlings resulting from the 2012 crossing, at a commercial greenhouse in Vista. Calif.

Asexual reproduction of the new cultivar 'Mardi Gras' was first performed in Vista, Calif., at a commercial greenhouse, by vegetative offsets, known as "peanuts" in April of 2013. 'Mardi Gras' has since produced multiple generations and has shown that the unique features of this cultivar are stable and reproduced true to type.

SUMMARY OF THE INVENTION

The cultivar 'MARDI GRAS' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'MARDI GRAS' These characteristics in combination distinguish 'MARDI GRAS' as a new and distinct *Echinopsis* cultivar:

1. Large flower in comparison to other similar *Echinopsis* hybrids of the Chamaelobivia group.
2. Petals exhibit a unique color combination of bright golden yellow gold contrasted by vivid vermillion mid-stripe
3. Extra petals contribute to a "cup and saucer" appearance of the flower
4. Flowering occurs at repeatedly times during the flowering season, rather than only one time, as compared to some other *Echinopsis* hybrids. Plant still flowering late August.
5. Very upright habit in contrast to many other *Echinopsis* hybrids with prostrate or pendulous habits.

Plants of the new cultivar 'MARDI GRAS' are similar to plants of the seed parent, in most horticultural characteristics, however, plants of the new cultivar 'MARDI GRAS' differ in the following;

1. 'Mardi Gras' produces flowers with underside of petals a contrasting color, whereas 'Yel 08 ' produces flowers of one color.
2. 'Mardi Gras' produces thicker apical spines than *Echinopsis* hybrid 'Yel 08'.
3. 'Mardi Gras' is more floriferous than *Echinopsis* hybrid 'Yel 08'.
4. 'Mardi Gras' produces more offsets than *Echinopsis* hybrid 'Yel 08'.
5. The flowers of 'Mardi Gras', have more petals per flower, than those of *Echinopsis* hybrid 'Yel 08'.

Plants of the new cultivar 'MARDI GRAS' are similar to plants of the pollen parent, in most horticultural characteristics, however, plants of the new cultivar 'MARDI GRAS' differ in the following;

1. 'Mardi Gras' has larger flowers than *Echinopsis* hybrid 'Wint 17'.
2. 'Mardi Gras' is more resistant to the pathogen *Bipolaris cactivora* (*Helminthosporium cactivorum*) than is *Echinopsis* hybrid 'Wint 17'
3. The flowers of *Echinopsis* hybrid 'Mardi Gras', due to the extra petals per flower, are more double-flowered than those of *Echinopsis* hybrid 'Wint 17'.
4. The flowers of the *Echinopsis* hybrid 'Mardi Gras' have at least two colors, whereas the flowers of the *Echinopsis* hybrid 'Wint 17' are one color.
5. The flowers of the 'Mardi Gras' can occur in several, very heavy flushes of flowers over a long span of flowering of 6-7 months, whereas the flowers of the *Echinopsis* hybrid 'Wint 17' occur in less heavy flushes, and the flowering span is only 3 months.

COMMERCIAL COMPARISON

Plants of the new cultivar 'MARDI GRAS' are comparable to the unpatented, commercial variety *Echinopsis* 'Fire Chief'. The two *Echinopsis* varieties are similar in most horticultural characteristics; however, the new variety 'MARDI GRAS' differs in the following:

1. *Echinopsis* hybrid 'Mardi Gras' produces flowers with at least two colors, whereas those of *Echinopsis* hybrid 'Fire Chief' are a monotone orange.
2. *Echinopsis* hybrid 'Mardi Gras' produces many more offsets than does *Echinopsis* hybrid 'Fire Chief', aiding in faster production of plants for commercial sales.
3. *Echinopsis* hybrid 'Mardi Gras' grows faster than does *Echinopsis* hybrid 'Fire Chief', accelerating production times in the commercial nursery.
4. The flower size of *Echinopsis* hybrid 'Mardi Gras' is larger than the flower size of *Echinopsis* 'Fire Chief'
5. *Echinopsis* hybrid 'Mardi Gras' exhibits several heavy flushes of flowers over a 6 to 7 month flowering span, whereas *Echinopsis* hybrid 'Fire Chief' does not produce these flower flushes, and the flowering span is only 1-2 months.

Plants of the new cultivar 'MARDI GRAS' can also be comparable to the unpatented commercial variety *Echinopsis* 'Westfield Alba'. The two *Echinopsis* varieties are similar in most horticultural characteristics; however, the new variety 'MARDI GRAS' differs in the following:

1. *Echinopsis* hybrid 'Mardi Gras' produces much larger "peanuts" (vegetative offsets) than does *Echinopsis* 'Westfield Alba', aiding in producing a saleable plant faster.
2. *Echinopsis* hybrid 'Mardi Gras' grows at a faster rate than does *Echinopsis* hybrid 'Westfield Alba', thereby enhancing production and reducing production time.
3. *Echinopsis* hybrid 'Mardi Gras' grows with a more upright morphology, unlike the prostrate, pendulous habit of *Echinopsis* hybrid 'Westfield Alba'.
4. *Echinopsis* hybrid 'Mardi Gras' produces flowers with at least 2 colors, whereas *Echinopsis* hybrid 'Westfield Alba' has monotone white flowers.
5. The flowers of *Echinopsis* hybrid 'Mardi Gras' are much larger than those of *Echinopsis* hybrid 'Westfield Alba'.

BRIEF DESCRIPTION OF THE PHOTOGRAPHS

The accompanying photographs illustrate in full color typical of plants of *Echinopsis* 'Mardi Gras' grown in a greenhouse in Vista, Calif. Age of the plant photographed is approximately 5 months from a vegetative offset, "peanut". The photographs were taken using conventional techniques and although colors may appear different from actual colors due to light reflectance it is as accurate as possible by conventional photographic techniques. All photographs provided by the breeder.

DETAILED BOTANICAL DESCRIPTION

Figure 1:
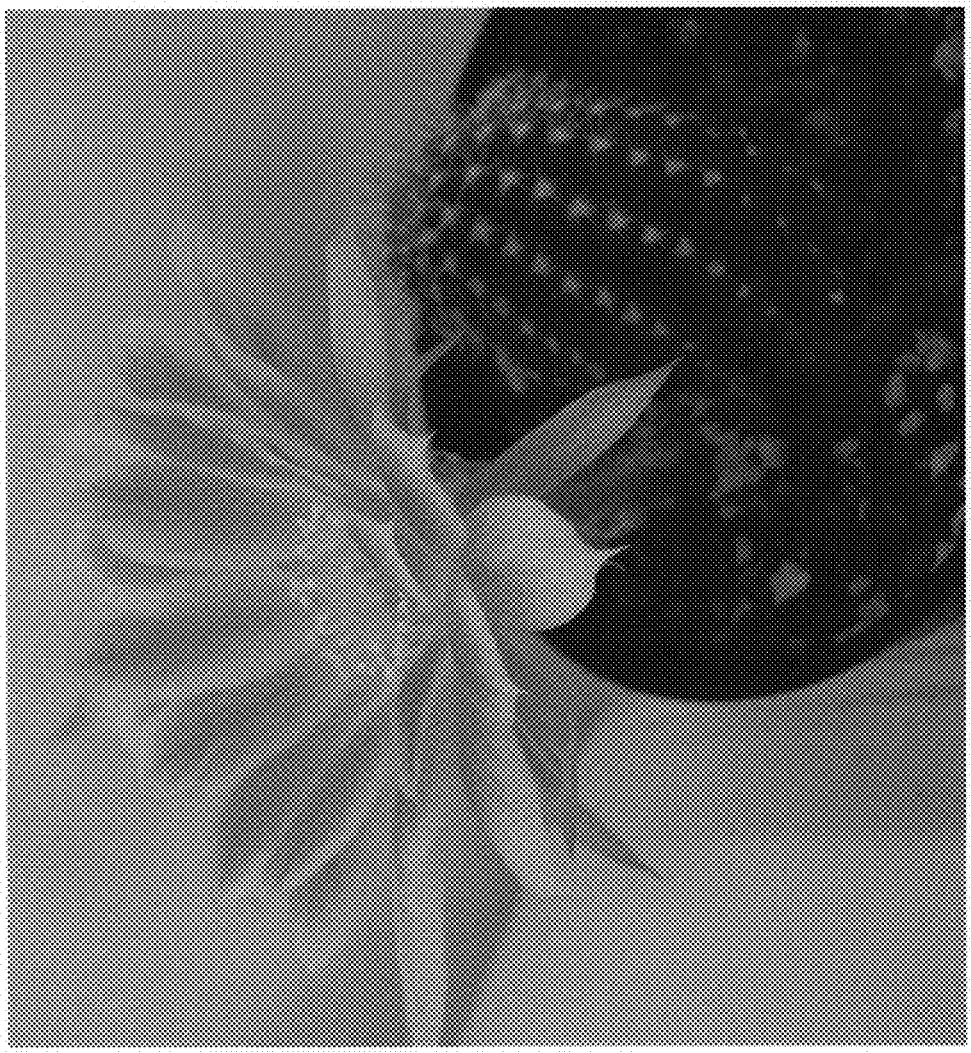
FIG. 1 illustrates in full color in close-up of the flower of *Echinopsis* hybrid 'Mardi Gras', grown in a greenhouse (approximately 3000 to 4000 foot candles) in Vista, Calif.
Figure 2:
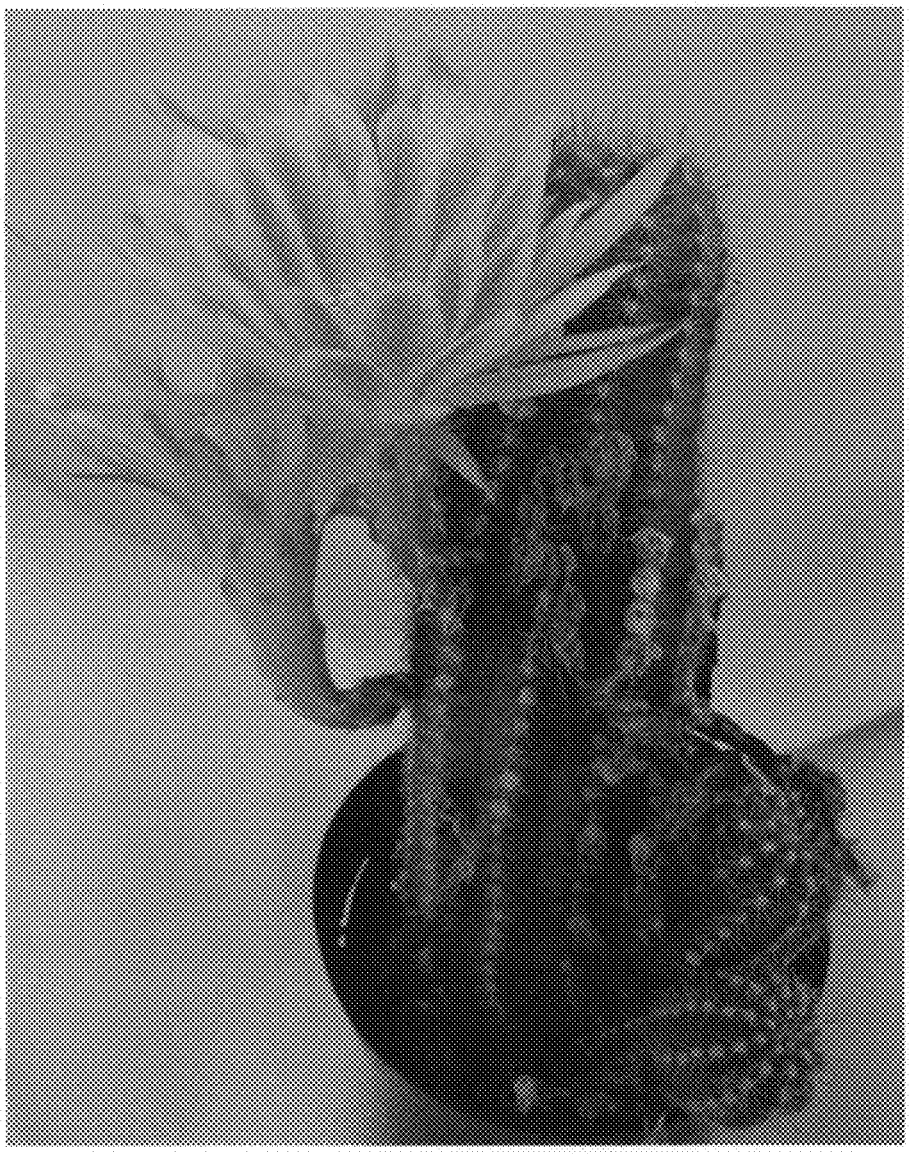
FIG. 2 illustrates in full color *Echinopsis* hybrid 'Mardi Gras' in 1 gallon pot with spent flowers.
Figure 3:
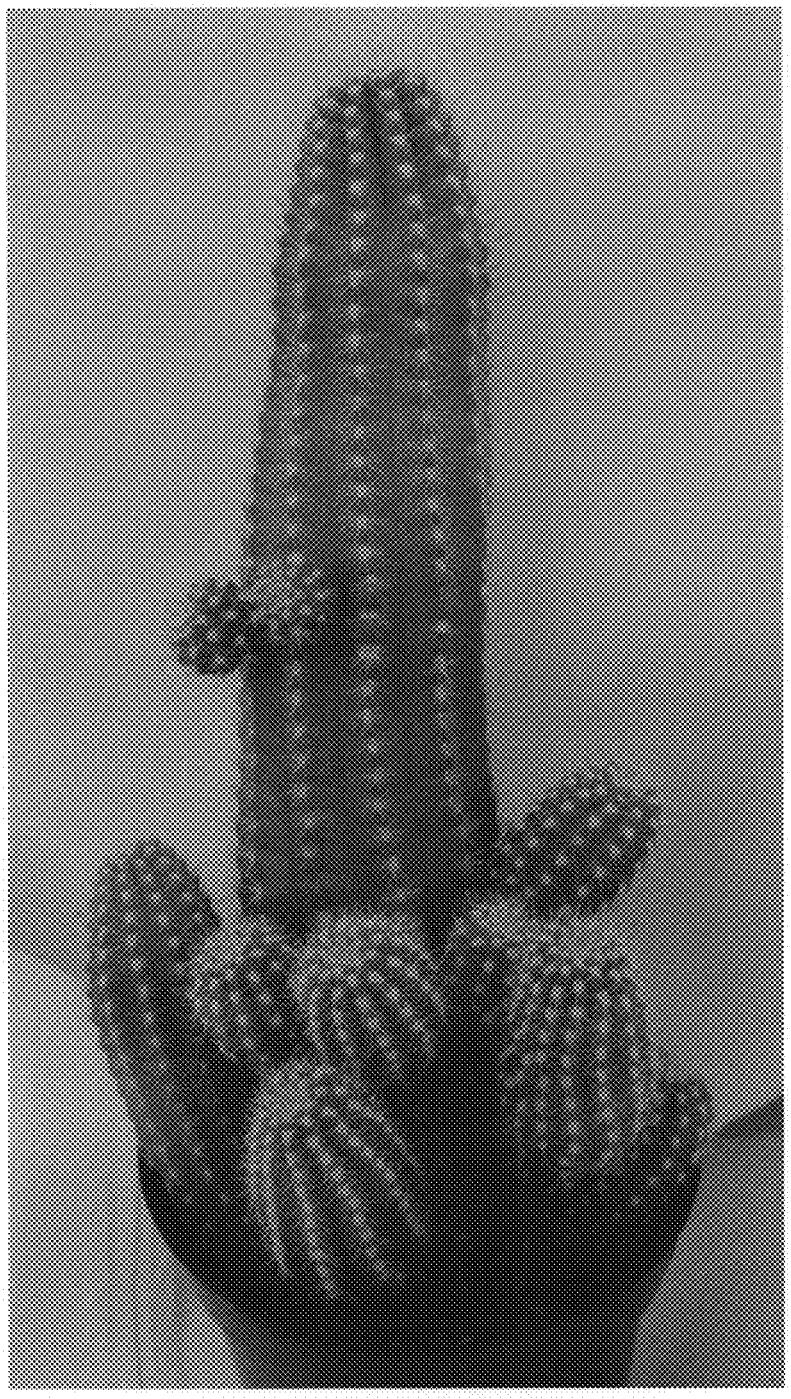
FIG. 3 illustrates in full color the plant morphology of *Echinopsis* hybrid 'Mardi Gras'

In the following description, color references are made to The Royal Horticultural Society Colour Chart, 2007, except where general terms of ordinary dictionary significance are used. The following observations and measurements describe 'Mardi Gras' plants in a commercial shadehouse in Vista, Calif. Temperatures ranged from 34° F. to 90° F. night and day. No artificial light, photoperiodic treatments or chemical treatments were given to the plants. Natural light conditions were approximately 3000-4000 foot candles of light. Measurements and numerical values represent averages of typical plant types.

Botanical classification: *Echinopsis hybrida* 'MARDI GRAS'.

PROPAGATION

Type of propagation typically used: Vegetative offsets known as "peanuts".

Time to develop roots: About 3 to 4 weeks at approximately 22° to 26° C.

Root description: Densely fibrous.

PLANT

Age of plant described: Approximately 4 to 5 months.

Container size of the plant described: 9 cm.

General plant description: Columnar, clump forming small cactus.

Growth habit: Upright, with a moderate quantity offsets forming clumps from base.

Plant spread: Approximately 6.0 to 9.0 cm, in a 4 inch pot approximately 4 months old.

Plant height: Approximately 9 to 20 cm.

Growth rate: Rapid.

Quantity of offsets: 2 to 10 present on a 4 inch pot, at the end of the growing season, in September.

Stem description:

*Diameter.*—4 to 5 cm.

*Height.*—9 to 20 cm.

*Color.*—Near RHS Green 143C.

Areole:

*Spacing.*—Approximately 5 mm apart on rib.

*Quantity.*—Approximately 500 per mature stem.

Spine/thorn description:

*Arrangement.*—Spines radially arranged. Average 12 ribs of spines vertically linear, nearly straight, minor spiral. Ribs spaced approximately 6 to 10 mm apart. Central spine approximately 6 mm, colored near Greyed-Purple 187A. Radial spines approximately 3 to 4 mm, colored near Orange-White 159C. Dense trichomes approximately 1 mm colored near Greyed-Yellow 161C.

FLOWER:

Natural flowering season: Approximately Spring until Fall in Southern California. Flowers constantly present, with 2 or more flushes of abundant flowering occurring.

Inflorescence type and habit: Open funnel form. Reduced tube length open, radial flower of 2 to 3 whorls.

Flower longevity on plant: 1 to 2 days.

Quantity of flowers: 4 inch pot has approximately 3 to 7 flowers and buds.

Individual flower size:

*Diameter.*—9 cm.

*Flower tube length.*—4 cm.

*Flower tube length.*—2.5 cm.

*Flower tube diameter at distal end.*—2.4 cm.

*Flower tube diameter at proximal end.*—1.0 cm.

Petals:

*Petal arrangement.*—Double or triple whorl.

*Length.*—Average range 2.8 to 3.2 cm.

*Width.*—0.9 cm.

*Quantity.*—Typically 20 to 25.

*Texture.*—Glabrous all surfaces.

*Appearance.*—Very shiny upper surface, moderately shiny lower surface.

*Margin.*—Entire.

*Tip shape.*—Cuspidate.

Color:

*Petals.*—When opening: Upper surface: Centermost streak near Red 46B, streak fading outwardly to Orange-Red 34A. Largest part of petal surface Yellow-Orange 14B, margin Yellow 12A. Lower surface: Centermost streak near Red 46B, streak fading outwardly to Orange-Red 34A. Largest part of petal surface Yellow-Orange 14B, margin Yellow 12A. Fully opened: Upper surface: Centermost streak near Red 44B, streak fading outwardly to Red 44B and 44C. Largest part of petal surface Yellow-Orange 14A, margin Yellow 12B. Center streak covers approximately ⅓ of width. Lower surface: Centermost streak near Red 44B, streak fading outwardly to Red 44B and 44C. Largest part of petal surface Yellow-Orange 14A, margin Yellow 12B. Center streak covers approximately ⅓ of width. Fading: Petals fading to, upper and lower: Faint centermost streak near Orange-Red N34B. Largest part of petal surface Yellow 12A.

*Flower tube color.*—Inner Surface: Near RHS Red 47B. Outer Surface: Near RHS Orange-White 159B, flushed Greyed-Orange N170D.

Bud:

*Shape.*—Oblong.

*Length.*—Approximately 7 cm.

*Diameter.*—Approximately 3.5 cm.

*Color.*—Near RHS Yellow 11B, dotted Orange 26A.

Peduncle:

*Length.*—Average 2.0 to 3.0 cm.

*Diameter.*—0.9 cm.

*Color.*—Adaxial section near RHS Greyed-Green 194C. Abaxial section near Orange-White 159A.

*Orientation.*—Straight, occurring at approximately 15° angle from stem.

*Strength.*—Very strong.

*Texture.*—Villous, moderately dense.

Sepals:

*Shape.*—Quantity per flower: Average 10.

*Length.*—Approximately shortest: Average 1.5 cm longest: 3.5 cm.

*Width.*—Approximately 0.4 cm.

*Margin.*—Entire.

*Texture.*—Glabrous and shiny all surfaces.

*Color, upper and lower surfaces.*—Near RHS Greyed-Red 181C, faint center streak near Greyed-Red 179C.

REPRODUCTIVE ORGANS

Stamens:

*Number.*—Average range 120 to 230.

*Filament length.*—Average 1.5 cm.

*Filament color.*—Near RHS Greyed-Red 181C and 181D, both colors present individually.

Anthers:

*Shape.*—Oblong.

*Length.*—Approximately 1.5 mm.

*Color.*—Near RHS Yellow 9C.

*Pollen.*—Color: Near RHS Yellow 10C. Quantity: Scant.

Pistil:

*Number.*—1.

*Length.*—Approximately 5.0 cm.

*Style.*—Length: Approximately 2.7 cm. Color: Near RHS Yellow-Green 144C.

*Stigma.*—Shape: 2 parted, each section folded inward. Size: 8 mm long, 5 mm wide. Color: Near RHS Yellow-Green 154A.

*Ovary.*—Length: 12 mm. Shape: Narrow oblong. Texture: Sericeous, sticky. Color: Near RHS Yellow-Green 145C.

OTHER CHARACTERISTICS

Fruits and seeds: Seed pods broad ovate, average range 1.2 to 1.5 cm in length, about 9 mm in diameter. Colored near Green 138B, sericeous, hairs near White 155A. Low to moderate seed production, seeds colored near Greyed-Orange 177A.

Temperature tolerance: USDA zones 10 and above.

Disease/pest resistance: More resistant to the pathogen *Bipolaris cactivora* (*Helminthosporium cactivorum*) Neither resistance nor susceptibility to other pathogens or pests of *Echinopsis* observed.

Drought tolerance: Extreme tolerance for drought.

What is claimed is:

1. A new and distinct cultivar of *Echinopsis* plant named 'MARDI GRAS' as herein illustrated and described.

* * * * *